(12) United States Patent
Braman et al.

(10) Patent No.: US 11,195,273 B2
(45) Date of Patent: Dec. 7, 2021

(54) DISEASE DETECTION FROM WEAKLY ANNOTATED VOLUMETRIC MEDICAL IMAGES USING CONVOLUTIONAL LONG SHORT-TERM MEMORY

(71) Applicant: INTERNATIONAL BUSINESS MACHINES CORPORATION, Armonk, NY (US)

(72) Inventors: Nathaniel Mason Braman, Cleveland Heights, OH (US); Ehsan Dehghan Marvast, Palo Alto, CA (US); David James Beymer, San Jose, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 16/600,009

(22) Filed: Oct. 11, 2019

(65) Prior Publication Data

US 2021/0110532 A1   Apr. 15, 2021

(51) Int. Cl.
*G06T 7/00*   (2017.01)
*G06K 9/66*   (2006.01)
(Continued)

(52) U.S. Cl.
CPC .............. *G06T 7/0012* (2013.01); *G06K 9/46* (2013.01); *G06K 9/66* (2013.01); *G06N 3/0454* (2013.01);
(Continued)

(58) Field of Classification Search
CPC ................. G06T 7/0012; G06T 11/003; G06T 2207/20081; G06T 2207/20084; G06K 9/46; G06K 9/66; G06N 3/0454
See application file for complete search history.

(56) References Cited

U.S. PATENT DOCUMENTS 10,347,010 B2   7/2019  Risman et al.
10,417,788 B2 *  9/2019  Risman .................. G06T 9/002
(Continued)

FOREIGN PATENT DOCUMENTS

CN   106250707 A   12/2016
CN   107103187 A    8/2017
(Continued)

OTHER PUBLICATIONS

Choi, Wook-Jin, and Tae-Sun Choi. "Automated pulmonary nodule detection based on three-dimensional shape-based feature descriptor." Computer methods and programs in biomedicine 113.1 (2014): 37-54. (Year: 2014).*
(Continued)

*Primary Examiner* — Pinalben Patel
(74) *Attorney, Agent, or Firm* — Michael Best & Friedrich LLP

(57) ABSTRACT

Systems and methods for developing a disease detection model. One method includes training the model using an image study and an associated disease label mined from a radiology report. The image study including a sequence of a plurality of two-dimensional slices of a three-dimensional image volume, and the model including a convolutional neural network layer and a convolutional long short-term memory layer. Training the model includes individually extracting a set of features from each of the plurality of two-dimensional slices using the convolutional neural network layer, sequentially processing the features extracted by the convolutional neural network layer for each of the plurality of two-dimensional slices using the convolutional long short-term memory layer, processing output from the convolutional long short-term memory layer for a sequentially last of the plurality of two-dimensional slices to
(Continued)

generate a probability of the disease, and updating the model based on comparing the probability to the label.

20 Claims, 8 Drawing Sheets
(7 of 8 Drawing Sheet(s) Filed in Color)

(51) Int. Cl.
    *G06K 9/46*     (2006.01)
    *G06T 11/00*     (2006.01)
    *G06N 3/04*     (2006.01)

(52) U.S. Cl.
    CPC .. *G06T 11/003* (2013.01); *G06T 2207/20081* (2013.01); *G06T 2207/20084* (2013.01)

(56) References Cited

U.S. PATENT DOCUMENTS

| | | | |
|---|---|---|---|
| 2016/0260211 A1* | 9/2016 | Gillies | G16H 50/30 |
| 2018/0005082 A1* | 1/2018 | Bluche | G06K 9/00409 |
| 2018/0089840 A1 | 3/2018 | Yan et al. | |
| 2018/0310870 A1* | 11/2018 | Givon | G16H 50/20 |
| 2019/0223725 A1 | 7/2019 | Lu et al. | |
| 2020/0074299 A1 | 3/2020 | Cho | |

FOREIGN PATENT DOCUMENTS

| | | |
|---|---|---|
| CN | 107392895 A | 11/2017 |
| CN | 107545269 A | 1/2018 |
| CN | 108470359 A | 8/2018 |
| CN | 109102491 A | 12/2018 |
| CN | 109147937 A | 1/2019 |
| CN | 109410194 A | 3/2019 |
| CN | 109635246 A | 4/2019 |
| CN | 110188936 A | 8/2019 |
| WO | 2017151757 A1 | 9/2017 |

OTHER PUBLICATIONS

Appendix P for U.S. Appl. No. 16/600,009, dated Jan. 20, 2020 (2 pages).
Shin, Hoo-Chang, et al., "Learning to Read Chest X-Rays: Recurrent Neural Cascade Model for Automated Image Annotation," Proceedings of the IEEE Conference on Computer Vision and Pattern Recognition, pp. 2497-2506, 2016.
Zheng, Jiannan, "Deep Learning with Limited Labeled Image Data for Health Informatics," PhD diss., University of British Columbia, 2018, 148 pages.
Yao, Li, et al., "Learning to Diagnose from Scratch by Exploiting Dependencies among Labels," arXiv preprint arXiv:1710.10501, 2017, 12 pages.
International Search Report and Written Opinion for Application No. PCT/IB2020/059467 dated Jan. 27, 2021 (12 pages).
United States Patent Office Action for U.S. Appl. No. 16/600,037 dated Jun. 16, 2021 (16 pages).
Baderaldeen et al., "Reproducibility of F18-FDG PET radiomic features for different cervical tumor segmentation methods, gray-level discretization, and reconstruction algorithm," J Appl Clin Med Phys, 2017, 18:(6): 32-48.

* cited by examiner

DISEASE DETECTION FROM WEAKLY ANNOTATED VOLUMETRIC MEDICAL IMAGES USING CONVOLUTIONAL LONG SHORT-TERM MEMORY

FIELD

Embodiments described herein generally relate to a deep learning framework for efficient learning from weak, but readily accessible, labels (for example, binary diagnoses of a particular disease) to detect diseases in image volumes. In particular, embodiments described herein provide a detection model that uses convolutional long short-term memory (Conv-LSTM) units to scan through an image volume and remember signatures of a disease on and between slices, wherein the detection model is trained using binary labels of the disease for a set of unannotated image volumes.

SUMMARY

Deep learning has demonstrated immense promise for enhanced, automated analysis of medical imaging, such as in computer aided diagnosis (CAD). For example, given a sufficiently large pool of training data, convolutional neural networks (CNN) can achieve exceptional results in disease detection. However, one obstacle to the development of deep learning-based CAD platforms in radiology is the need for large, annotated medical image datasets. Particularly in the case of three-dimensional (3D) imaging modalities, such as computed tomography (CT), it is often prohibitively onerous for radiologists to provide sufficient manual annotations for the training of deep models. Therefore, training a disease detection model using a large data set of annotated samples is often practically infeasible and there is a considerable need for deep learning frameworks that use imaging data in the form its exists clinically: abundant but lacking annotation. Beyond being able to leverage large unannotated large unannotated data sets for the development of disease detection models, such approaches allow easy fine-tuning to a new institution using the institution's available imaging data. This ability is important given known challenges of successfully deploying deep learning systems in a new institution.

For example, many lung disease detection approaches rely on manual delineation of a region of interest (ROI) on an image volume for both training and evaluation of a trained model. To address the above issues regarding limited availability of annotated image sets, some approaches use weakly labeled imaging data. In particular, some systems automatically subsample a 3D volume containing a labeled disease into randomly selected two-dimensional (2D) patches and perform supervised clustering to categorize patches into disease positive states. Other systems use a multiple instance learning (MIL) approach to summarizing disease diagnosis, such as lung disease diagnosis, across a group of examples from an imaging volume containing some portion of positive examples.

A majority of these approaches, however, rely on classification by so-called "hand-crafted" quantitative imaging features for the characterization of diseases. Such approaches are limited by a list of pre-defined imaging features chosen for a classification task and experience minimal improvement as the pool of training data increases into the thousands. Additionally, the patch approach uses only a small portion of the image volume (for example, fifty 2D patch subsamples per scan) thereby limiting the imaging data available for learning. In addition, because patches are randomly samples and a disease may not be present in the entire ROI, such as a lung, this approach will inevitable include healthy patches that correspond to an overall disease positive status. Such healthy samples from diseased patients are likely to confound both training and testing. Similarly, MIL approaches summarize a disease status across multiple samples from a volume, but lack context regarding the spatial relationships between those samples and their interactions.

Thus, to address these and other problems with existing approaches, embodiments described here provide a solution for using weakly, yet easily obtainable, annotated volumetric medical images by treating the 3D image as a time-sequence of 2D images. As evidenced in this application, this solution can be used to detect emphysema in lung cancer screening using low-dose CT images. Emphysema, associated with shortness of breath and elevated cancer risk, often manifests as ruptured air sacs within only a portion of the lung volume. Embodiments described herein provide a deep learning framework utilizing convolutional long short-term memory (LSTM) and MIL to "scan" through an image volume for emphysema without the need for expert annotations of diseased regions. For annotations, embodiments described herein use only binary labels (non-diseased state or diseased state), which can be extract from readily available radiology reports. Using this approach, a model can be trained to identify emphysema while minimizing the risk of false positives. Beyond emphysema, embodiments described herein are applicable to other disease and abnormality (collectively referred to as "diseases" herein) detection problems where the availability of volumetric imaging data exceeds the capacity of radiologists to provide manually delineated ground truth but labels can be easily mined from radiology reports or other sources.

One of the advantages of the approach described herein is the capability to leverage the large availability of volumetric clinical imaging data to train a CAD system without the need for labor-intensive manual annotations performed by a radiologist. In some embodiments, these systems can run in the background as a second check on radiologists' diagnosis (only requiring input when the system detects a potentially missed diagnosis) and could reduce false negatives by 20-50%. Embodiments described herein also address the drawbacks of other systems described above. In particular, unlike CAD approaches described above that leverage hand-crafted quantitative imaging features, the deep learning-based approach described herein discovers optimal image patterns to distinguish disease states within the training set and, thus, is unconstrained by a pool of manually-defined imaging features. As a result, the performance of this approach continues to improve from larger and larger sets of training data. Therefore, this approach can be trained using minimally annotated data that is readily obtained and derives benefit from the abundance of that data. The approach described herein also circumvents the issue of mislabeled training patches inherent in the patching approaches described above. In particular, while embodiments described herein analyze samples containing both healthy and diseased states, evaluation of the entire volume at once ensures that every sample labeled disease positive will actually contain diseased features (tissue). Unlike a pure MIL approach, embodiments described herein consider the individual slices as a continuous sequence, thus considering spatial relationships between slices and updating a prediction of disease status as an imaging volume is scanned.

For example, some embodiments provide a system that includes a computing device equipped with software configured to (1) accept 3D imaging volumes consisting of stacked 2D radiological images, (2) manipulate the volumes for efficient processing, and (3) analyze the image volumes through a neural network architecture that analyzes the 2D slices of a volume sequentially and outputs a predicted probability that a disease state or other aberration is present. The neural network is trained to identify the disease using a large number of imaging volumes that are only weakly labeled (for example, only have a binary diagnostic status for one or more disease states/abnormalities within an entire volume) without any guidance on the location of that disease within that volume. The neural network includes (a) 2D convolutional operations that learn and detect image patterns on individual 2D slices, (b) convolutional long short-term memory (LSTM) units, which scan through a 3D volume slice-by-slice and detect spatial patterns and their variations throughout a 3D volume, (c) a distributed dense operation that outputs a 0 to 1 prediction of disease status corresponding to the convolutional LSTM scan at each slice, and, optionally, (d) a MIL bag probability function, which summarizes the network's predictions as it analyzes the 3D volume into a single prediction for the entire volume.

For example, one embodiment provides a system for developing a disease detection model. The system includes one or more electronic processors. The one or more electronic processors are configured to train the disease detection model using an image study and an associated disease label mined from a radiology report generated for the image study. The image study includes a sequence of a plurality of two-dimensional slices of a three-dimensional image volume, and the disease detection model including a convolutional neural network layer and a convolutional long short-term memory layer. Training the disease detection model includes individually extracting a set of features from each of the plurality of two-dimensional slices using the convolutional neural network layer, sequentially processing the set of features extracted by the convolutional neural network layer for each of the plurality of two-dimensional slices using the convolutional long short-term memory layer, processing output from the convolutional long short-term memory layer for a sequentially last of the plurality of two-dimensional slices to generate a probability of the disease, comparing the probability to the label, and updating the disease detection model based on the comparison. The one or more electronic processors are also configured to, after the disease detection model is trained, apply the disease detection model to a new image study to generate a probability of the disease for the new image study.

Another embodiment provides a method for developing a disease detection model. The method includes training, with one or more electronic processors, the disease detection model using an image study and an associated disease label mined from a radiology report generated for the image study. The image study including a sequence of a plurality of two-dimensional slices of a three-dimensional image volume, and the disease detection model including a convolutional neural network layer and a convolutional long short-term memory layer. Training the disease detection model includes individually extracting a set of features from each of the plurality of two-dimensional slices using the convolutional neural network layer, sequentially processing the feature extracted by the convolutional neural network layer for each of the plurality of two-dimensional slices using the convolutional long short-term memory layer, processing output from the convolutional long short-term memory layer for a sequentially last of the plurality of two-dimensional slices to generate a probability of the disease, comparing the probability to the label, and updating the disease detection model based on the comparison. The method also includes, after the disease detection model is trained, applying the disease detection model to a new image study to generate a probability of the disease for the new image study.

Yet another embodiment provides a non-transitory computer-readable medium storing instructions that, when executed by one or more electronic processors, perform a set of functions. The set of functions includes training the disease detection model using an image study and an associated disease label mined from a radiology report generated for the image study. The disease label includes a binary label of whether a patient associated with the image study was diagnosed with the disease, and the image study includes a sequence of a plurality of two-dimensional slices of a three-dimensional image volume. The disease detection model includes a convolutional neural network layer and a convolutional long short-term memory layer. Training the disease detection model includes individually extracting a set of features from each of the plurality of two-dimensional slices using the convolutional neural network layer, sequentially processing the set of features extracted by the convolutional neural network layer for each of the plurality of two-dimensional slices using the convolutional long short-term memory layer, processing output from the convolutional long short-term memory layer for a sequentially last of the plurality of two-dimensional slices to generate a probability of the disease, comparing the probability to the label, and updating the disease detection model based on the comparison. The set of functions further including, after the disease detection model is trained, applying the disease detection model to a new image study to generate a probability of the disease for the new image study.

A further embodiment provides a system for developing a disease detection model. The system comprises one or more electronic processors. The one or more electronic processors are configured to train the disease detection model using an image study and an associated disease label mined from a radiology report generated for the image study. The image study includes a sequence of a plurality of two-dimensional slices of a three-dimensional image volume, and the model includes a convolutional neural network layer and a convolutional long short-term memory layer. Training the disease detection model includes individually extracting a set of features from each of the plurality of two-dimensional slices using the convolutional neural network layer, sequentially processing the set of features extracted by the convolutional neural network layer for each of the plurality of two-dimensional slices using the convolutional long short-term memory layer, processing output from the convolutional long short-term memory layer for each of the plurality of two-dimensional slices to generate a probability of the disease, comparing the probability to the label, and updating the disease detection model based on the comparison. The one or more electronic processors are also configured to, after the disease detection model is trained, apply the disease detection model to a new image study to generate a probability of the disease for the new image study.

An additional embodiment provides a method for developing a disease detection model. The method includes training, with one or more electronic processors, the disease detection model using an image study and an associated disease label mined from a radiology report generated for the image study. The image study includes a sequence of a plurality of two-dimensional slices of a three-dimensional image volume, and the disease detection model includes a convolutional neural network layer and a convolutional long short-term memory layer. Training the disease detection model includes individually extracting a set of features from each of the plurality of two-dimensional slices using the convolutional neural network layer, sequentially processing the set of features extracted by the convolutional neural network layer for each of the plurality of two-dimensional slices using the convolutional long short-term memory layer, processing output from the convolutional long short-term memory layer for each of the plurality of two-dimensional slices to generate a probability of the disease, comparing the probability to the label, and updating the disease detection model based on the comparison. The method also includes, after the disease detection model is trained, applying the disease detection model to a new image study to generate a probability of the disease for the new image study.

Some embodiments also non-transitory computer-readable medium storing instructions that, when executed by one or more electronic processors, perform a set of functions. The set of functions includes training the disease detection model using an image study and an associated disease label mined from a radiology report generated for the image study. The disease label includes a binary label of whether a patient associated with the image study was diagnosed with the disease, and the image study includes a sequence of a plurality of two-dimensional slices of a three-dimensional image volume. The disease detection model includes a convolutional neural network layer and a convolutional long short-term memory layer, training the disease detection model includes individually extracting a set of features from each of the plurality of two-dimensional slices using the convolutional neural network layer, sequentially processing the set of features extracted by the convolutional neural network layer for each of the plurality of two-dimensional slices using the convolutional long short-term memory layer, processing output from the convolutional long short-term memory layer for each of the plurality of two-dimensional slices to generate a probability of the disease, comparing the probability to the label, and updating the disease detection model based on the comparison. The set of functions also includes, after the disease detection model is trained, applying the disease detection model to a new image study to generate a probability of the disease for the new image study.

Other aspects of the embodiments will become apparent by consideration of the detailed description and accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

One or more embodiments are described and illustrated in the following description and accompanying drawings. These embodiments are not limited to the specific details provided herein and may be modified in various ways. Furthermore, other embodiments may exist that are not described herein. Also, the functionality described herein as being performed by one component may be performed by multiple components in a distributed manner. Likewise, functionality performed by multiple components may be consolidated and performed by a single component. Similarly, a component described as performing particular functionality may also perform additional functionality not described herein. For example, a device or structure that is "configured" in a certain way is configured in at least that way, but may also be configured in ways that are not listed. Furthermore, some embodiments described herein may include one or more electronic processors configured to perform the described functionality by executing instructions stored in non-transitory, computer-readable medium. Similarly, embodiments described herein may be implemented as non-transitory, computer-readable medium storing instructions executable by one or more electronic processors to perform the described functionality. As used in the present application, "non-transitory computer-readable medium" comprises all computer-readable media but does not consist of a transitory, propagating signal. Accordingly, non-transitory computer-readable medium may include, for example, a hard disk, a CD-ROM, an optical storage device, a magnetic storage device, a ROM (Read Only Memory), a RAM (Random Access Memory), register memory, a processor cache, or any combination thereof.

In addition, the phraseology and terminology used herein is for the purpose of description and should not be regarded as limiting. For example, the use of "including," "containing," "comprising," "having," and variations thereof herein is meant to encompass the items listed thereafter and equivalents thereof as well as additional items. The terms "connected" and "coupled" are used broadly and encompass both direct and indirect connecting and coupling. Further, "connected" and "coupled" are not restricted to physical or mechanical connections or couplings and can include electrical connections or couplings, whether direct or indirect. In addition, electronic communications and notifications may be performed using wired connections, wireless connections, or a combination thereof and may be transmitted directly or through one or more intermediary devices over various types of networks, communication channels, and connections. Moreover, relational terms such as first and second, top and bottom, and the like may be used herein solely to distinguish one entity or action from another entity or action without necessarily requiring or implying any actual such relationship or order between such entities or actions.

Figure 1:
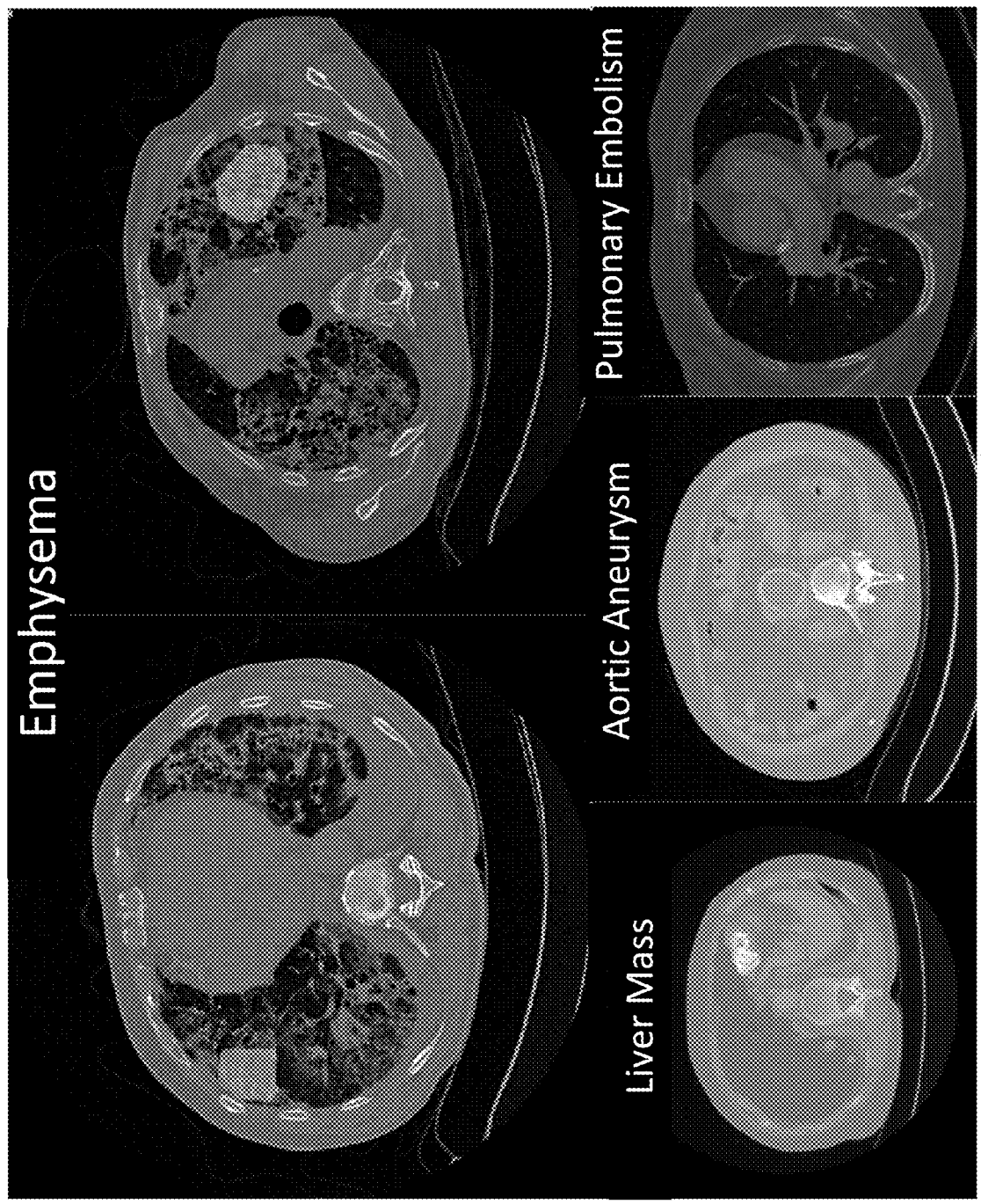
FIG. 1 illustrates example annotations used to train a deep learning model for detection of various abnormalities on computer tomography (CT) images.

As described above, deep learning-based diagnosis in radiology requires large, manually-annotated imaging datasets. However, despite the availability of clinical data, expert annotation of volumetric imaging is prohibitively onerous. In particular, manually delineating boundaries on image volumes is often too time-consuming for radiologists to perform in the quantity required for the training of deep models. For example, FIG. 1 illustrates example annotations (see color annotations) used to train a deep learning model for detection of various abnormalities on computer tomography (CT) images. Accordingly, in many cases, such as in chest CT, scans may be frequently performed and readily available, but may not contain any labeling beyond the contents of associated radiology reports. Thus, this presents a substantial obstacle to using large set of clinical imaging data when training a model.

As also noted above, emphysema is a respiratory disease caused by the rupturing of air sacs within the lungs and is associated with shortness of breath and cancer risk. Emphysema is frequently diagnosed via CT images of a patient's lung. However, emphysema's variety of presentations and localizations (may only appear in a portion of the lung volume) on CT images present a challenge in training deep models to detect emphysema from unlabeled data. For example, although visible as regions of low attenuation on lung CTs, emphysema can be missed as an incidental diagnosis when patients receive standard dose CT scans to primarily evaluate conditions outside the lung.

To address these challenges, some detection systems use a multiple instance learning (MIL) approach with hand-crafted feature or deep learning to identify emphysema and other lung diseases. These MIL approaches use a weakly-labeled supervised learning strategy for leveraging training data with imprecise, global labels. In MIL approaches, a classifier is applied to a set of samples whose individual labels are unknown but can be grouped into a labeled "bag." Model training and inference is then performed based on a label and prediction for the entire bag. For instance, a clinically positive CT volume could be considered as a positive bag, with each 2D slice forming a sample. The presence of emphysema on any individual slice is unknown, but it must be present on one or more slices in the bag if a patient is disease positive.

While MIL can be effective at training a model and summarizing its predictions across a number of weakly annotated samples, it also possesses several disadvantages. First, MIL fails to account for spatial context between the samples in a bag. Isolated positive samples throughout a volume are more likely to represent false positives due to noise as compared to a series of consecutive slices all resembling emphysema, but the implications of this proximity is considered in a MIL setting. Second, MIL requires a pooling operation that summarizes sample-level predictions into a single prediction for the bag. This summarization is performed using naïve methods (for example, average or max of sample predictions), which can be inflexible and impact the instances in which a MIL model detects or misses disease, regardless of the strength of the underlying classifier.

Accordingly, embodiments described herein provide a deep learning framework for efficient learning from weak, but readily accessible, labeled training data to detect diseases/abnormalities in image volumes. In particular, one embodiment includes a convolution long short-term memory implementation (LSTM) (Conv-LSTM). Recurrent neural network approaches, such as long short term memory (LSTM) are capable of interpreting and summarizing patterns among correlated samples, and Conv-LSTM is a variant of LSTM that uses convolutional operations to distinguish variations in spatial patterns. For instance, Conv-LSTM excels in detecting spatiotemporal patterns. Rather than applying Conv-LSTM to time series image data, embodiments described herein apply Conv-LSTM to scan through a series of consecutive slices of an imaging volume to learn patterns of disease without manual annotations of its locations. This approach allows the detection of disease on and between slices, storing such detections through multiple bidirectional passes through a volume and output as a final set of features characterizing overall disease presence. Thus, the embodiments described herein improves on other approaches by considering spatial relationships between slices and succinctly summarizing findings without requiring a potentially reductive pooling approach. As described below through the disclosed experimental data, the Conv-LSTM approach provides an effective and versatile solution for disease detection and can make efficient use of weakly-labeled image volumes for training and tuning.

Accordingly, the Conv-LSTM implementation uses convolutional Conv-LSTM to "scan" through an imaging volume for a disease without expert annotation. This approach allows for detection of disease patterns on and between two-dimensional (2D) slices without a potentially reductive bag pooling operation. In particular, like the 2D convolution MIL implementation, this implementation includes convolutional operations to recognize patterns within individual slices. However, this implementation also includes multiple convolutional LSTM units throughout the network, which consider the slices of a volume as a sequence. Features extracted from each slice individually by previous convolutional layers are fed one at a time into a convolutional LSTM moving in a first direction through the volume (for example, a forward direction from head to toe) and, subsequently, a convolutional LSTM moving in a second, opposite direction (for example, a backward from toe to head), followed by another set of forward-backward convolution LSTM processing. The convolutional LSTM has the capability to "remember" image patterns associated with a disease from previous slices, as well as identify changes between slices that are indicative of a disease. For each item in a sequence, the convolutional LSTM outputs a set of features based on patterns within the image and its own internal memory. For the last convolutional LSTM unit, the set of features corresponding to the last slice analyzed is connected to a dense layer, which outputs a probability of disease (emphysema) based on the information accumulated across multiple scans of the imaging volume.

Figure 2:
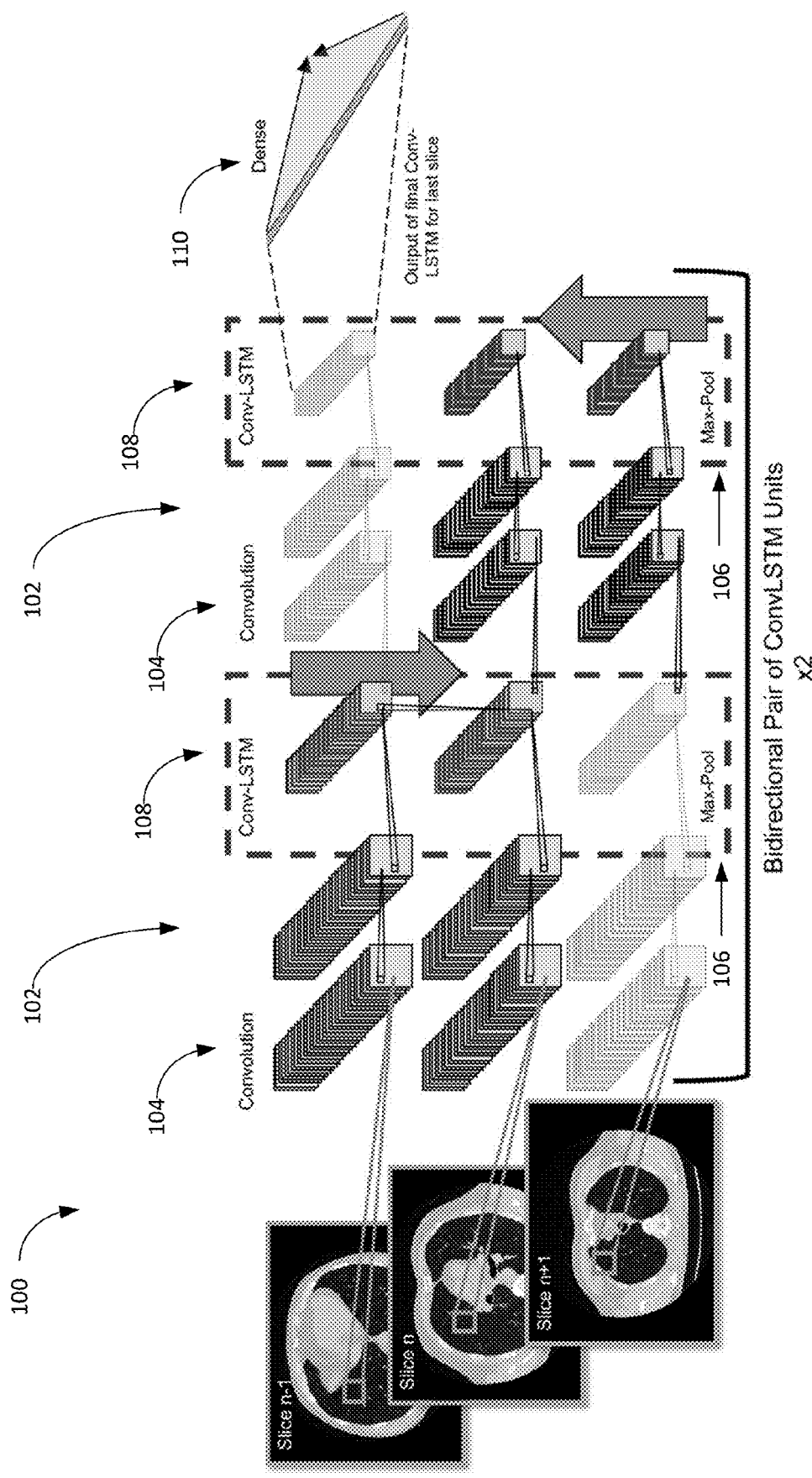
FIG. 2 illustrates a convolutional long short-term memory (Conv-LSTM) network for disease detection in weakly annotated volumes.

For example, FIG. 2 illustrates a Conv-LSTM network 100 for disease detection in weakly annotated image volumes according to one embodiment. As illustrated in FIG. 2, the network 100 includes four units 102. In particular, FIG. 2 illustrates one bidirectional pair of units (total of two units), wherein the network 100 includes two such pairs. Each unit 102 features two 2D convolutional layers 104, which extract features from each 2D slice of a 3D volume separately. Each pair of 2D convolutional layers 104 is followed by max pooling 106 and a Conv-LSTM layer 108. The Conv-LSTM layer 108 processes the volume slice-by-slice. Each 2D convolutional layer 104 has a kernel size of 3×3 and rectified linear unit (ReLU) activation, followed by batch normalization. The outputs from the convolutional layers for each slice are then processed sequentially by a Conv-LSTM layer 108 with, in some embodiments, tan h activation and hard sigmoid recurrent activation that uses a kernel size of 3×3.

The layers within a unit 102 share the same number of filters and process the volume in an ascending or descending order. For example, in some embodiments, the four units 102 have the following dimensionality and directionality: a first unit 102 applies 32 filters to the image volume in an ascending order, a second unit 102 applies 32 filters to the image volume in a descending order, a third unit 102 applies 64 filters to the image volume in an ascending order, and a fourth unit 102 applies 64 filters to the image volume in a descending order. The last Conv-LSTM layer 108 in the network 100 outputs a single set of features, which represents the network's findings after processing through the imaging volume multiple times. A fully-connected layer with sigmoid activation (a sigmoid-activated dense layer 110) then computes disease probability, such as a probability of emphysema. In some embodiments, regions indicating an emphysema diagnosis were additionally identified for post-hoc analysis via visual attention with guided back-propagation.

As is known in the art, LSTM frameworks process input at various time steps and includes a hidden state, representing short-term memory, and a cell track, representing long-term memory. At each time step, the LSTM performs three operations. First, the LSTM performs a forget operation that erases information from the long term memory. Next, the LSTM portions a remember operation that stores new information to the long-term memory, and, third, performs an update and output operation, that synthesizes the input, the hidden state (short term memory) and the long term memory into an output and a new hidden state. Conv-LSTM expands the LSTM to operate on sequential image data by making the LSTM operations convolutional.

Figure 3:
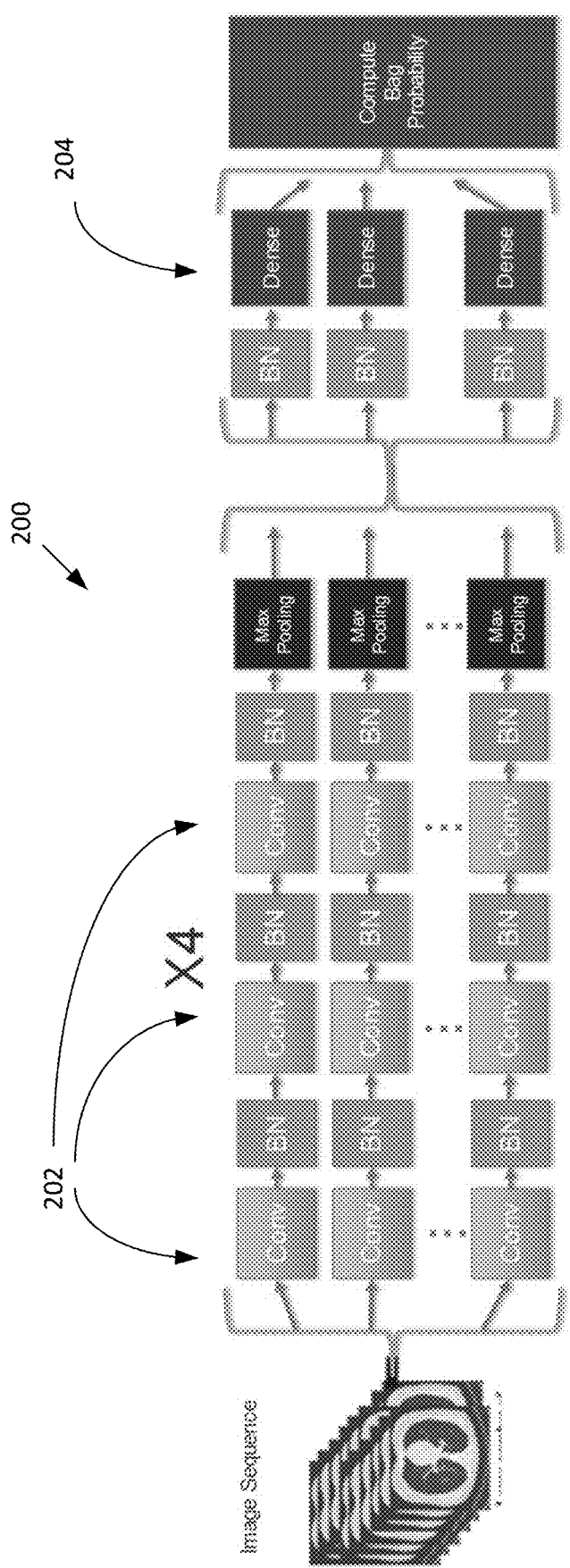
FIG. 3 illustrates a two-dimensional (2D) convolutional multiple instance learning (MIL) network for disease detection according to some embodiments.

As noted above, an experiment was conducted to assess the performance of the Conv-LSTM implementation. As part of the experiment, performance of the Conv-LSTM implementation was compared to a 2D convolutional MIL configuration and a three-dimensional (3D) convolutional neural network (CNN). FIG. 3 illustrates the 2D convolutional MIL network or configuration according 200 to some embodiments. In this configuration 200, each 2D slice of an imaging volume is passed individually through an identical network that performs 2D convolution operation, interspersed with normalization (e.g., batch normalization ("BN") is applied to each slice) and pooling operations to reduce the dimensionality of the model and facilitate training. The convolution network 200 outputs a series of image features from many nested convolution operations 202 for each slice of the volume. A dense layer 204 then summarizes these features into a 0 to 1 probability that a disease (for example, emphysema) is present in a given slice. Processing the whole volume with this network 200 produces N disease probabilities, where N is the number of slices within the imaging volume. In the final layer, a MIL summary function summarizes the slice level probabilities into a single probability of the disease across the entire volume.

Accordingly, in this network 200, each slice of an image volume is a sample from a bag in a MIL scheme, processed by a purely convolutional 2D network. Several different algorithmic approaches can be used as a means of computing overall volume probability, such as, for example, a maximum individual slice probability, a product of slice probabilities weighted toward a positive diagnostic finding, a means probability across the slices, or the like. For example, in some embodiments, the overall probability, P, is calculated from N instances with individual probabilities of emphysema, p using one of the below equations:

Mean Pooling:

$$P = \frac{1}{N}\sum_{i=1}^{N} p_i$$

Max Pooling:

$$P = \max(p_i)$$

Product Pooling:

$$P = 1 - \Pi_{i=1}^{N}(1-p_i)$$

Although not illustrated in the figures, a 3D CNN has a similar structure as the structure to the 2D convolutional MIL network 300 but has a single dense layer and no pooling operation on the final convolutional layer.

The experiment used a total of 55,673 non-contrast low-dose CT volumes from 11,095 unique participants enrolled in the National Lunch Screen Trial (NLST). 5,056 participants who were diagnosed with emphysema across the three years of the study were included as positive samples and 6,039 participants who were not diagnosed with emphysema were included as negative samples. 80% of patients were used for model training, with balanced distribution of emphysema positive and negative patients. 39,387 volumes from 7,100 patients were used to directly learn model parameters, which 9,755 volumes from 1,776 patients were used to tune hyper-parameters. The remaining 2,219 patients (578 emphysema positive, 1585 emphysema negative), each with three annual scans for a total of 6,511 volumes, were held out for independent testing. Volumes were resized to 128×128×35, corresponding to an average slice spacing of 9 millimeters.

The experiment sought to compare the performance of a Conv-LSTM with traditional learning schemes suited to weakly annotated image volumes. To reduce time and resources required to train all models, a reduced pilot cohort was utilized for this comparison consisting of 8,794 low-dose CT volumes from 6,648 unique patients. 4,197 volumes (from 3,166 patients) and 2,434 volumes (from 1,319 patients) were used for training and validation, respectively. 2,163 volumes from 2,163 patients (578 emphysema positive, 1585 emphysema negative) were used for testing. Each model was trained for 50 epochs with a learning rate of 1e-3.

Figure 4:
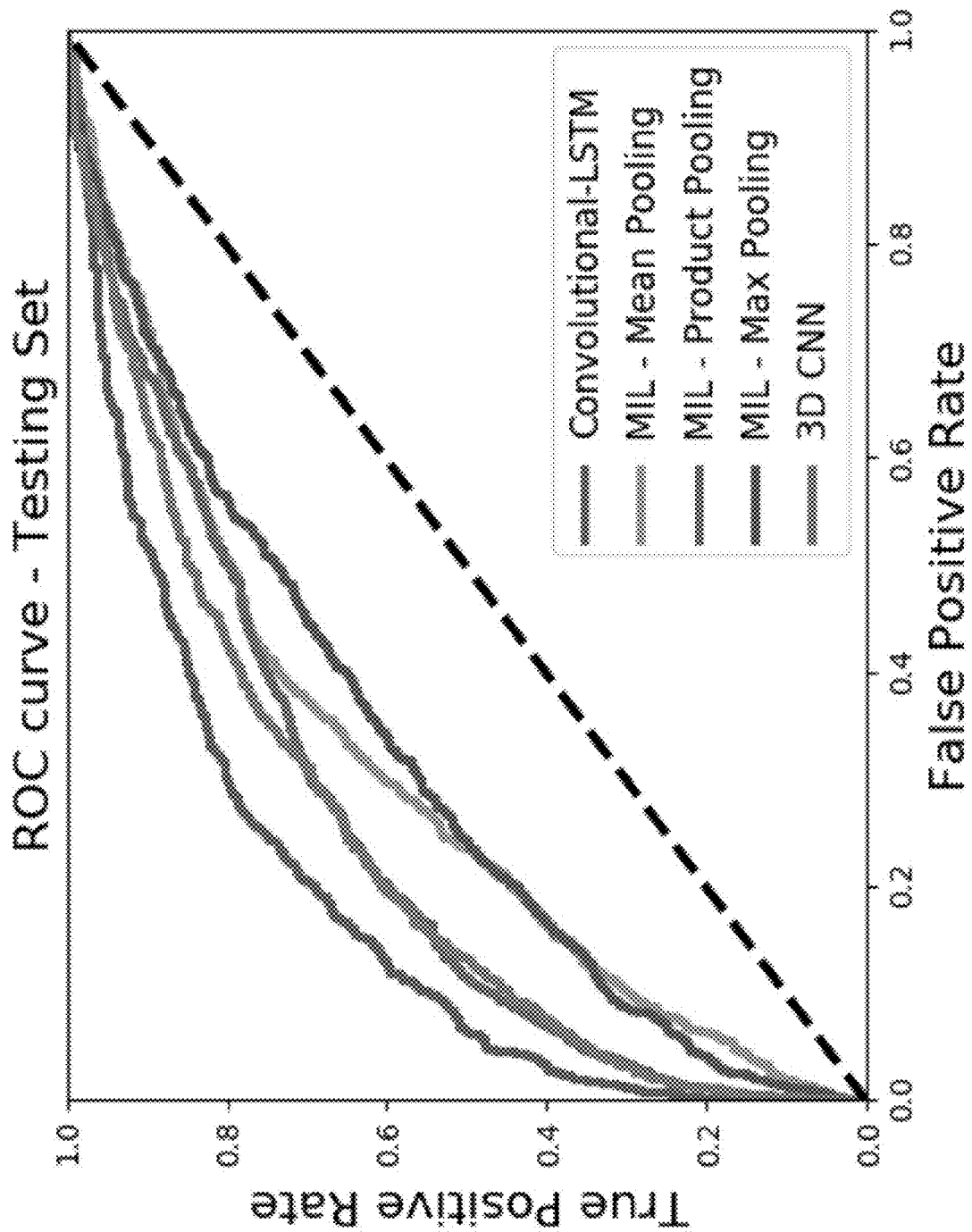
FIG. 4 illustrates performance of the Conv-LSTM network of FIG. 2 and the 2D convolution MIL network of FIG. 3 for emphysema detection in a testing set using receiver operating characteristic (ROC) curves.

The Conv-LSTM implementation strongly identified emphysema when trained with only weakly annotated imaging volumes, achieving an area under the receiver operating characteristic curve (AUC) of 0.83. As illustrated in FIG. 4, this implementation outperformed all MIL configurations and the 3D CNN (see Table 1 below), despite 110,000 and 57,000 fewer parameters than these architectures respectively.

TABLE 1

| | Kernels | Parameters | AUC | Sensitivity | Specificity | F1 |
|---|---|---|---|---|---|---|
| MIL-Max Pool | 64 | 1,011,393 | 0.69 | 0.59 | 0.68 | 0.63 |
| MIL-Mean Pool | 64 | 1,011,393 | 0.70 | 0.76 | 0.57 | 0.66 |
| MIL-Product Pooling | 64 | 1,011,393 | 0.76 | 0.61 | 0.79 | 0.69 |
| 3D CNN | 36 | 958,213 | 0.77 | 0.61 | 0.80 | 0.69 |
| Conv-LSTM | 32 | 901,793 | 0.83 | 0.77 | 0.74 | 0.75 |

Having demonstrated superior performance in detecting emphysema as compared to other techniques, the Conv-LSTM implementations was retrained using the full NLST cohort for a total of 300 epochs. Each epoch consisted of 200 steps with a batch size of 20, randomly selected from the pool of nearly 40,000 training volumes. During training, random flipping along the x, y, and z axes was applied to further augment the data and 50% dropout was applied to the neutrons of the final dense layer to prevent overfitting. The model was trained using binary cross entropy loss and the ADAM optimizer, with an initial learning rate of 1e-4. If validation loss failed to decrease after 20 consecutive epochs, the learning rate was reduced by half. Models were trained using 2 Tesla P100 GPUs, with training time taking approximately 27 hours.

When trained using the full training cohort, Conv-LSTM performance increased to AUC=0.909 within the testing set (n=6,511). At the optimal cutoff corresponding to the Youden index identified within the validation cohort, testing sensitivity was 80.9% and specificity was 86.3% (F1=0.836).

A total of 3,361 NLST patients were excluded from the model training and evaluation in previous experiments due to a changing emphysema diagnosis during the three years the patients were followed. Of these, 926 patients received a positive diagnosis for emphysema in year 1, but a negative diagnosis in year 2 or year 3 (but not both). Given that emphysema is a chronic disease, these evaluations likely represent a missed diagnosis and, thus, present the opportunity to evaluate a model's capability to reduce false negatives. For example, the model can be applied at the operating point to evaluate performance among challenging cases missed by radiologists.

Sensitivity among likely clinical false negatives was 70.6%; near the value observed at the same cutoff in the testing set (80.9%). Thus, the Conv-LSTM model retained strong performance in a cohort consisting of the most challenging emphysema diagnoses. Average predicted probability of emphysema presence was 0.63±0.370, as compared to 0.754±0.328 and 0.171±0.229 among emphysema positive and negative patients in the testing cohort.

1,405 patients were obtained from the Lung Tissue Research Consortium (LTRC) with standard dose CT scans acquired in the supine position during expiration. Training and validation cohorts were 800 and 200 patients, respectively. The model was tested on scans from 405 patients. Manual annotations of emphysema boundaries were also available for some patients in this cohort, but were not used during training. Instead, the manual annotations were used to compare with visual saliency maps from the Conv-LSTM network.

The Conv-LSTM models can also be used to easily perform fine-tuning for unfamiliar imaging data at new institutions through transfer learning on a limited cohort of standard dose CT. Transfer learning generally refers to starting from a model trained on dataset or task and making small adjustments to the trained model to optimize performance of the model among a second type of data or task (usually utilizing a much smaller pool of data than was used to initially train the model). Transfer learning can allow models to be developed that achieve strong results in unfamiliar data using a smaller amount of training data because the model starts from an existing trained model. Low dose CT (such as in NLST) is typically used as a screening approach for lunch cancer. Standard dose CT, however, might be ordered for a larger variety of reasons including multiple organ sites. Since the primary purpose of these exams might not be to assess the lung, automated emphysema detection possesses significant potential for incidental detection of a disease in regions outside of radiologist's focus. The Conv-LSTM models described herein could, however, be retrained from a limited cohort of unannotated volumes with an unfamiliar acquisition protocol (standard dose CT). Thus, these models present a viable mechanism for accounting for previously un-encountered sources of variability when deploying deep models, such as between institutions, by simple transfer learning on limited datasets of available clinical imaging and diagnostic information. Thus, these models could serve as an accurate and flexible system to check radiologists' diagnoses and detect missed disease detection, such as emphysema.

Figure 5:
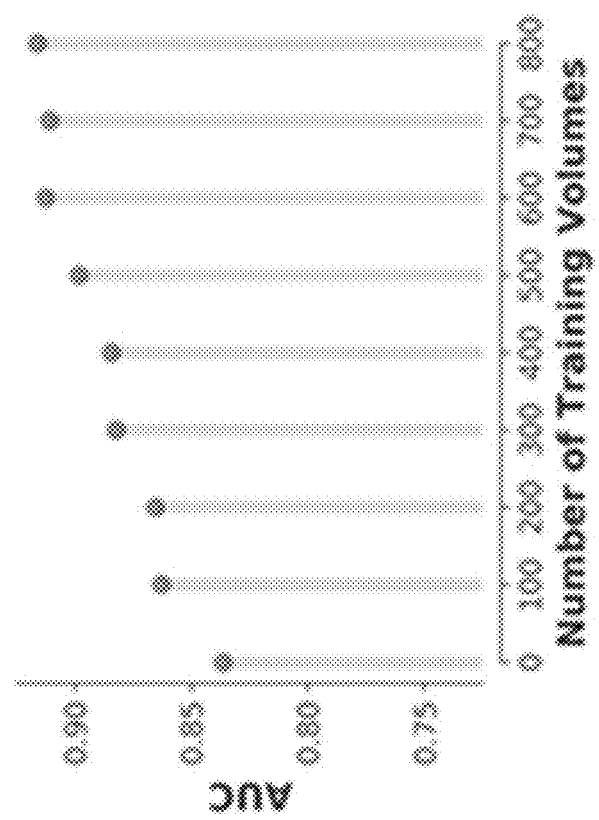
FIG. 5 illustrates emphysema detection performance of the Conv-LSTM network of FIG. 2 through transfer learning to standard dose computed tomography (CT) with variable training set sizes.

For example, FIG. 5 depicts performance for transfer learning using standard dose CT training cohorts of various size. When the mode was applied directly to standard dose CT without transfer learning, validation AUC was 0.836. Best results were obtained utilizing the full 800 training patients (validation AUC was 0.916), but as few of 500 patients can product similarly strong performance of AUC greater than or equal to 0.90.

When tuned with n=800 and applied to the testing cohort (n=405), AUC improved to 0.945. The operating point identified in validation corresponded to sensitivity of 84.4% and specificity was 92.7% (F1=0.886) in testing. Example visual attention maps demonstrate strong concordance with manual emphysema annotations (see FIG. 6), and could be used to help localize diagnoses.

Accordingly, as described above, a challenge to deep learning applications in medical imaging is the need for large annotated medical imaging datasets for model training. Deep learning schemes capable of learning efficiently from data with weak, easily-obtainable labels, such as the methods and systems described herein, circumvent this limitation. For example, using the methods and systems described herein, deep computer-aided diagnosis (CAD) platforms that rely on only binary diagnostic labels for training can be rapidly developed using massive clinical imaging datasets and easily adapted to new clinical contexts from available data (for example, fine-tuning to new institutions or acquisition protocols).

Figure 6:
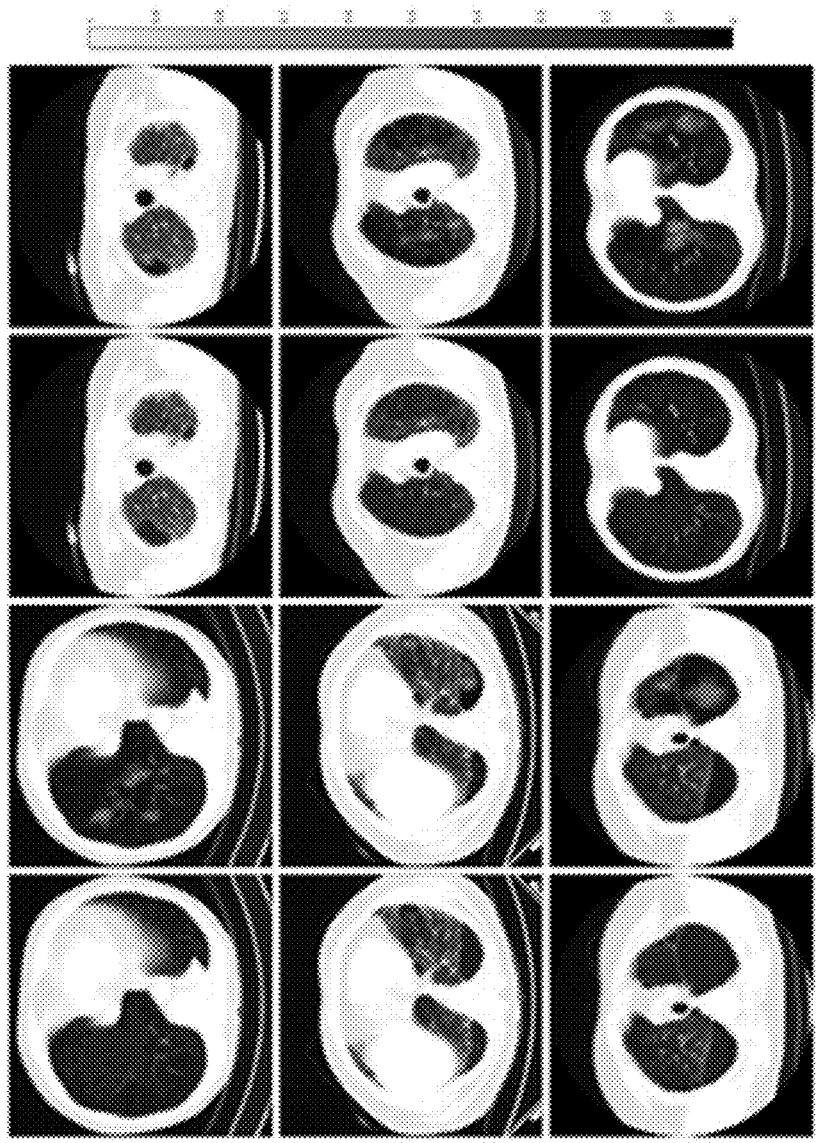
FIG. 6 illustrates spatial alignment between manually annotated emphysema ground truth and visual attention maps associated with the Conv-LSTM network of FIG. 2.

In particular, embodiments described herein provide a convolutional recurrent framework that is capable of learning disease signatures from only weakly annotated image volumes. Traditional approaches for weakly supervised learning problems, such as MIL, operate on "bags" of spatially distributed image samples, but fail to consider spatial relationships between samples and can be hindered by a potentially restrictive bag pooling operation. The convolutional long short-term memory (Conv-LSTM) implementations described herein address these shortcoming by processing a volume sequentially for a presence of disease in a portion of the scanned region and updating a single feature set characterizing disease presence throughout an entire volume. As described above, using this approach provides a powerful tool for detecting emphysema, especially as compared to 3D CNN and MIL (a weakly supervised learning strategy coupled with a 2D CNN) in a variety of configurations. In particular, the implementations described herein, in some embodiments, require no time-consuming annotation or manual processing of imaging data, which enables the use of expansive clinical datasets of weakly labeled image volumes. Also, in some embodiments, as illustrated in FIG. 6, visual attention maps for the proposed network implementations substantially overlapped with ground truth for the small portion of standard dose CT scans with emphysema presence manually delineated by a radiologist, despite no use of manual annotations during model training. For example, FIG. 6 demonstrates spatial alignment between manually annotated emphysema ground truth (left, red) and visual attention maps (right) generated by the Conv-LSTM models described herein. Thus, these models can localize disease patterns across a number of different emphysema presentations even when trained from only volume-level binary training labels.

Figure 7:
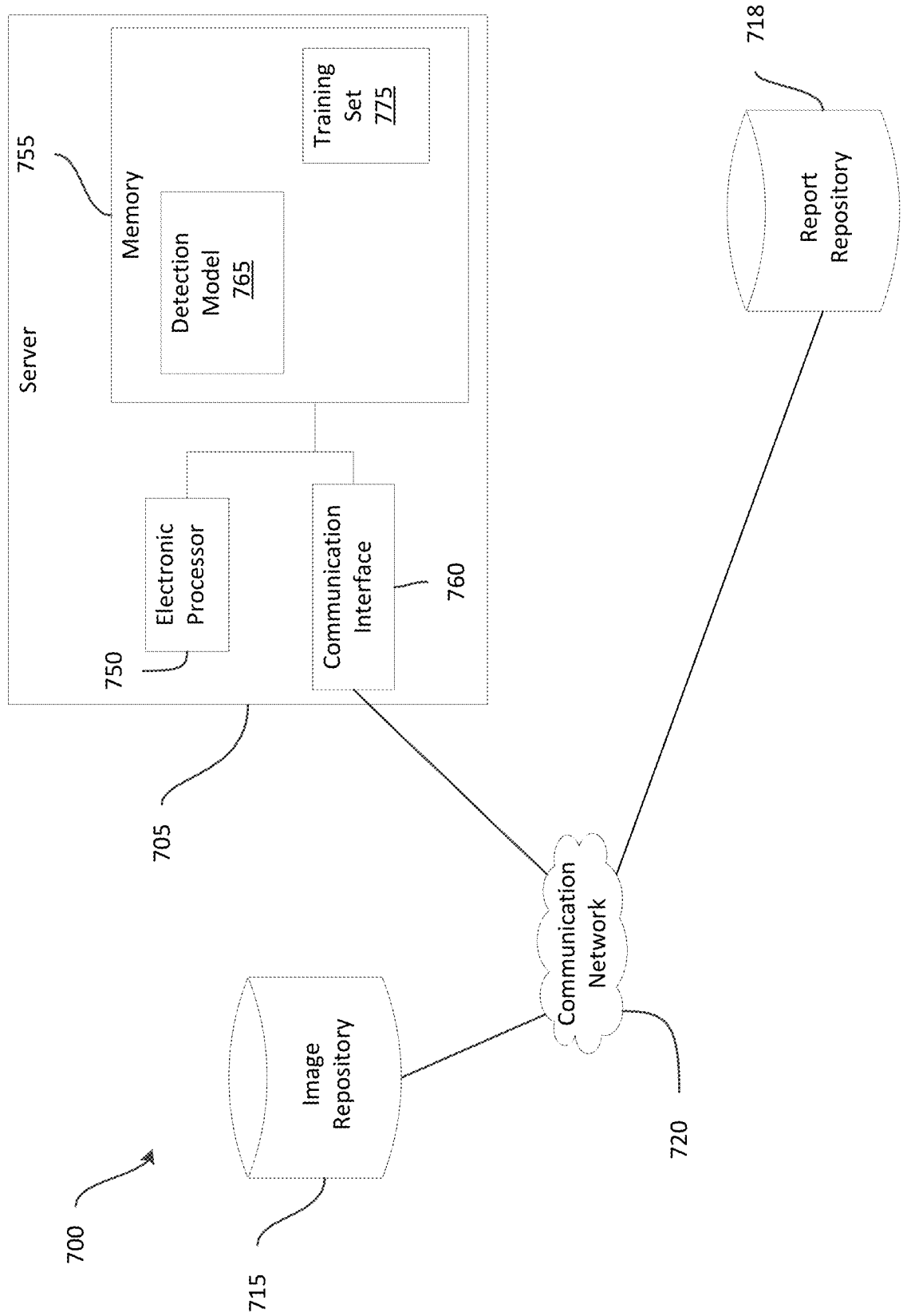
FIG. 7 schematically illustrates a system for implementing the Conv-LSTM network of FIG. 2 according to some embodiments.

It should be understood that the functionality described herein can be performed via one or more computing devices, such as one or more servers. For example, FIG. 7 illustrates a system 700 for training a disease detection model from weakly labeled volumetric imaging using the Conv-LSTM implementations described herein according to some embodiments. As illustrated in FIG. 7, the system 700 includes a server 705, an image repository 715, and a report repository 718. The server 705, the image repository 715, and the report repository 718 communicate over one or more wired or wireless communication networks 720. Portions of the wireless communication networks 720 may be implemented using a wide area network, such as the Internet, a local area network, such as a Bluetooth™ network or Wi-Fi, and combinations or derivatives thereof. It should be understood that the system 700 may include more or fewer servers and the single server 705 illustrated in FIG. 7 is purely for illustrative purposes. For example, in some embodiments, the functionality described herein is performed via a plurality of servers in a distributed or cloud-computing environment. Also, in some embodiments, the server 705 may communicate with multiple image repositories or multiple reports repositories. Furthermore, in some embodiments, an image repository may be combined with a report repository and, in some embodiments, one or more of these repositories may be combined with the server 705. Also, in some embodiments, the components illustrated in the system 700 may communicate through one or more intermediary devices (not shown).

In some embodiments, three dimensional images volumes are stored in the image repository 715. The image repository 715 may be, for example, a picture archiving and communication system (PACS), a cloud storage environment, or the like. The three dimensional image volumes stored in the image repository 715 are generated by an imaging modality (not shown), such as an X-ray computed tomography (CT) scanner, a magnetic resonance imaging (MRI) scanner, or the like. In some embodiments, the image repository 715 may also be included as part of an imaging modality. As noted above, the imaging volumes stored in the image repository are unannotated.

The report repository 718 stores radiology reports for image studies (images volumes), such as the image volumes stored in the image repository 715. For example, the report repository 718 may include a radiology information system (RIS), an electronic medical record (EMR) system, a hospital information system (HIS), or the like. Also, in some embodiments, the report repository 718 includes a PACS and may be combined with the image repository.

As illustrated in FIG. 7, the server 705 includes an electronic processor 750, a memory 755, and a communication interface 760. The electronic processor 725, the memory 730, and the communication interface 760 communicate wirelessly, over wired communication channels or buses, or a combination thereof. The server 705 may include additional components than those illustrated in FIG. 7 in various configurations. For example, in some embodiments, the server 705 includes multiple electronic processors, multiple memory modules, multiple communication interfaces, or a combination thereof. Also, it should be understood that the functionality described herein as being performed by the server 705 may be performed in a distributed nature by a plurality of computers located in various geographic locations. For example, the functionality described herein as being performed by the server 705 may be performed by a plurality of computers included in a cloud computing environment.

The electronic processor 750 may be a microprocessor, an application-specific integrated circuit (ASIC), and the like. The electronic processor 750 is generally configured to execute software instructions to perform a set of functions, including the functions described herein. The memory 755 includes a non-transitory computer-readable medium and stores data, including instructions executable by the electronic processor 750. The communication interface 760 may be, for example, a wired or wireless transceiver or port, for communicating over the communication network 720 and, optionally, one or more additional communication networks or connections.

As illustrated in FIG. 7, the memory 755 of the server 705 includes a detection model 765 and a training set 775. It should be understood that, in some embodiments, the functionality described herein as being provided by the detection model 765 (or the training thereof) may be distributed and combined in various configurations, such as through multiple separate software applications. The detection model 765 includes a Conv-LSTM model as described above, which is trained via the training set 775. As described above, the training set includes unannotated image volumes (retrieved or accessed from the image repository 715) and associated binary labels (retrieved or accessed from the report repository 718). After the detection model 765 is trained via the training data 775, the detection model 765 can be used to output a prediction of a disease, such as emphysema per the examples above.

In some embodiments, after a model has been trained with a pool of data, the model does not need access to that data to operate. For example, the process of training a network essentially involves learning a set of operations to perform a task from the training data. The learned set of operations (often referred to as the "weights" of the neural network) can be stored to repeat the task, without storing the training data itself. In some embodiments, there are two possible implementations for using the network and, in some embodiments, neither of these implementations requires continued storage of the training set. For example, in one implementation, the network can be trained with a training set provided by one source (which may be trained using training data from one or more institutions). The trained model can then be made available on a server for the same source or a different source (such as at a hospital or on the cloud). In this implementation, patient data does not need to be retained on the server.

In another implementation, an institution may use their own weakly labeled data to optimize the original weights to achieve optimized performance for the institution (a process called transfer learning as described above). In this implementation, a training set might be provided by the institution (for example, a hospital) on a server to perform transfer learning. However, after new weights have been learned through transfer learning, the training set does not need to be retained in memory (on the server).

It should also be understood that the systems and methods described herein are not limited to emphysema or even lung diseases or abnormalities, but can be used with various types of volumetric image data when binary labels are available even when expert annotations are not (the availability of volumetric imaging data and radiology reports exceeds the capacity of radiologists to provide manual annotations). Furthermore, the implementations described herein can be used with various slice spacing and even with image volumes with an arbitrary number of slices (all scans used do not necessarily need to have the same number of slices).

Figure 8:
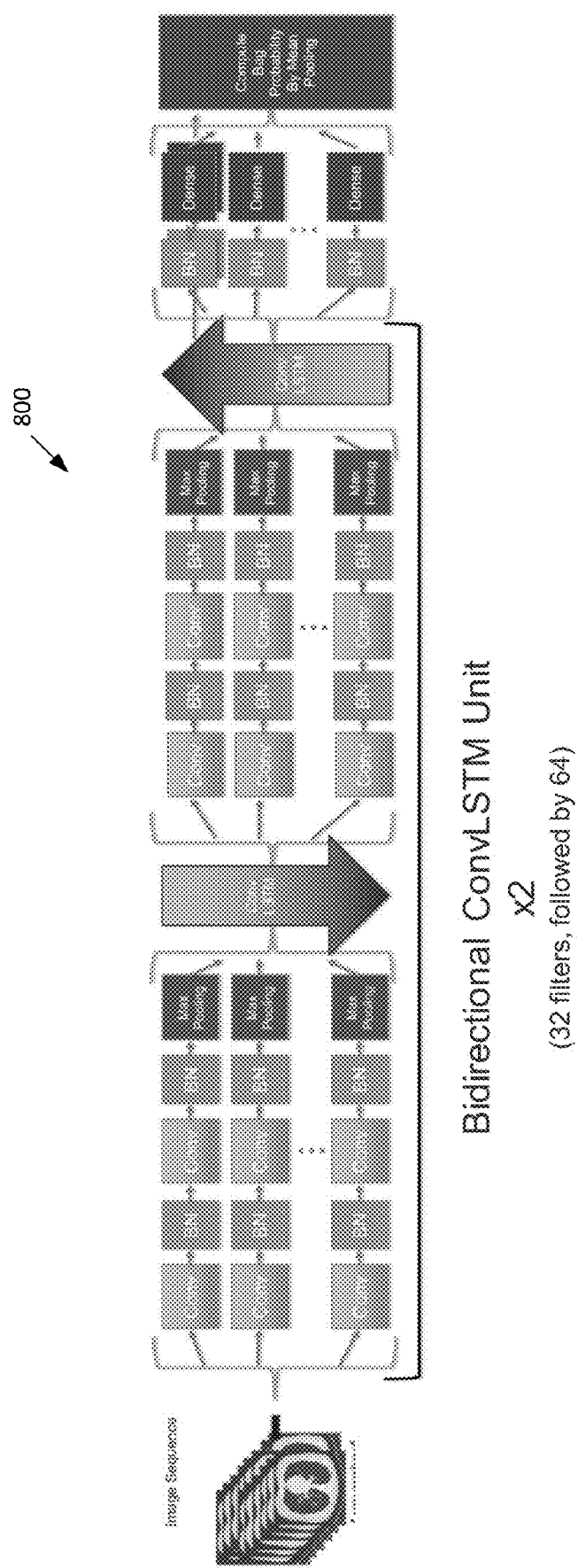
FIG. 8 illustrates a Conv-LSTM network combined with MIL according to some embodiments.

Also, other implementations of the Conv-LSTM network can be used in various situations. For example, in some embodiments, the Conv-LSTM network can be combined with MIL. This approach weights predictions generated on a per-slice basis as a network scans an image volume. FIG. 8 illustrates an example network 800 of this Conv-LSTM and MIL combination. In the network 800 (similar to the Conv-LSTM approach implemented via the network 100), the imaging volume is processed through a series of convolutional and convolutional LSTM operations. However, rather than taking only the output from the final sequence analyzed by the last convolutional LSTM, the output for each slice from each convolutional LSTM unit is incorporated into a single prediction with MIL. In particular, an identical dense layer can be connected to each sequential output of the convolutional LSTM to provide N predictions of disease likelihood and, as in the 2D convolutional MIL implementation, an overall disease probability can be computed for the entire volume, such as by computing a mean of the slice probabilities. In some embodiments, any of the equations described above with respect to FIG. 3 and the MIL network 300 can be used to calculate the overall probability.

As compared to the Conv-LSTM implementation, the Conv-LSTM MIL implementation achieved a better performance in a validation set and, thus, in some situations, may represent the optimal configuration. In particular, in a held-out testing set, the Conv-LSTM MIL implementation had an AUC of 0.8751, a cutoff 1 sensitivity (50% sensitivity) of 53.32%, a cutoff 1 specificity (50% sensitivity) of 96.05%, a cutoff 2 sensitivity (20% sensitivity) of 23.80%, and a cutoff 2 specificity (20% sensitivity) of 99.52%. Additionally, within a cohort of scans in which a diagnosis of emphysema was likely missed despite positive diagnoses in previous years (scans that were likely especially challenging to diagnose), the Conv-LSTM MIL implementation achieved 42.76% and 15.98% sensitivity at each cutoff. In addition, when the Conv-LSTM MIL model was retrained and evaluating on a full validation set (n=9,775), the model had an AUC of 0.8482, a cutoff 1 specificity (50% sensitivity) of 96.49% and a cutoff 2 specificity (20% sensitivity) of 99.57%.

It should be understood that, in some embodiments, more than one disease may be detected as part of building the training set given binary labels of each disease (for example, by detecting multiple labels. In this implementation, each detected disease may be used to generate a separate model as described above. Furthermore, in some embodiments, the network described above may be modified such that the network outputs a set of predictions for multiple diseases. For example, a model could be developed (through the use of multiple labels) that detects emphysema, cancer, and pneumonia. In this implementation, the model could output a vector ([p_emphysema, p_cancer, p_pneumonia]). Accordingly, in this implementation, the network could be trained to simultaneously detect all three of these diseases at the same time.

Various features and advantages of some embodiments are set forth in the following claims.

What is claimed is:

1. A system for developing a disease detection model, the system comprising:
one or more electronic processors configured to:
train the disease detection model using an image study and an associated disease label mined from a radiology report generated for the image study, the image study including a sequence of a plurality of two-dimensional slices of a three-dimensional image volume, the disease detection model including a convolutional neural network layer and a convolutional long short-term memory layer, wherein training the disease detection model includes
individually extracting a feature of each of the plurality of two-dimensional slices using the convolutional neural network layer;
sequentially processing, as time series image data, the feature extracted by the convolutional neural network layer for each of the plurality of two-dimensional slices using the convolutional long short-term memory layer;
processing output from the convolutional long short-term memory layer for a sequentially last of the plurality of two-dimensional slices to generate a probability of the disease;
comparing the probability to the label;
updating the disease detection model based on the comparison; and
after the disease detection model is trained, apply the disease detection model to a new image study including a sequence of a plurality of two-dimensional slices of a three-dimensional image volume to generate a probability of the disease for the new image study.

2. The system of claim 1, wherein the disease label includes a binary label of whether a patient associated with the image study was diagnosed with the disease.

3. The system of claim 1, wherein the probability of the disease is a probability of emphysema.

4. The system of claim 1, wherein the plurality of two-dimensional slices include a series of computed tomography (CT) images including a chest.

5. The system of claim 1, wherein the three-dimensional image volume does not include any annotations.

6. The system of claim 1, wherein sequentially processing the feature extracted by the convolution neural network layer for each of the plurality of two-dimensional slices using the convolution long short-term memory layer includes detecting spatial patterns and variations through the three-dimensional image volume.

7. The system of claim 1, wherein the disease detection model includes two bi-directional pairs of units, wherein each unit includes the convolutional layer and the convolutional long short-term memory layer.

8. The system of claim 1, wherein the two bi-directional pairs of units includes a first unit applying 32 filters to the three-dimensional image volume in an ascending order of the plurality of two-dimensional slices, a second unit applying 32 filters to the three-dimensional image volume in a descending order of the plurality of two-dimensional slices, a third unit applying 64 filters to the three-dimensional image volume in the ascending order, and a fourth unit applying 64 filters to the three-dimensional image volume in the descending order.

9. The system of claim 1, wherein the one or more processors are configured to process the output from the convolutional long short-term memory layer for the sequentially last of the plurality of two-dimensional slices to generate a probability of the disease by outputting a single set of features from the sequentially last of the plurality of two-dimensional slices to a sigmoid-activated dense layer.

10. The system of claim 1, wherein the disease detection model further includes a max pooling layer for the convolutional long short-term memory layer.

11. A method for developing a disease detection model, the method comprising:
    training, with one or more electronic processors, the disease detection model using an image study and an associated disease label mined from a radiology report generated for the image study, the image study including a sequence of a plurality of two-dimensional slices of a three-dimensional image volume, the disease detection model including a convolutional neural network layer and a convolutional long short-term memory layer, wherein training the disease detection model includes
        individually extracting a feature of each of the plurality of two-dimensional slices using the convolutional neural network layer;
        sequentially processing, as time series image data, the feature extracted by the convolutional neural network layer for each of the plurality of two-dimensional slices using the convolutional long short-term memory layer;
        processing output from the convolutional long short-term memory layer for a sequentially last of the plurality of two-dimensional slices to generate a probability of the disease;
            comparing the probability to the label;
            updating the disease detection model based on the comparison; and
    after the disease detection model is trained, applying the disease detection model to a new image study including a sequence of a plurality of two-dimensional slices of a three-dimensional image volume to generate a probability of the disease for the new image study.

12. The method of claim 11, wherein the disease label includes a binary label of whether a patient associated with the image study was diagnosed with the disease.

13. The method of claim 11, wherein the probability of the disease is a probability of emphysema.

14. The method of claim 11, wherein the plurality of two-dimensional slices include a series of computed tomography (CT) images including a chest.

15. The method of claim 11, wherein the 3-dimensional image volume does not include any annotations.

16. The method of claim 11, wherein the disease detection model includes two bi-directional pairs of units, wherein each unit includes the convolutional layer and the convolutional long short-term memory layer.

17. The method of claim 11, wherein processing the output from the convolutional long short-term memory layer for the sequentially last of the plurality of two-dimensional slices to generate a probability of the disease includes outputting a single set of features from the sequentially last of the plurality of two-dimensional slices to a sigmoid-activated dense layer.

18. Non-transitory computer-readable medium storing instructions that, when executed by one or more electronic processors, perform a set of functions, the set of functions comprising:
    training the disease detection model using an image study and an associated disease label mined from a radiology report generated for the image study, the disease label including a binary label of whether a patient associated with the image study was diagnosed with the disease and the image study including a sequence of a plurality of two-dimensional slices of a three-dimensional image volume, the disease detection model including a convolutional neural network layer and a convolutional long short-term memory layer, wherein training the disease detection model includes
        individually extracting a feature of each of the plurality of two-dimensional slices using the convolutional neural network layer;
        sequentially processing, as time series image data, the feature extracted by the convolutional neural network layer for each of the plurality of two-dimensional slices using the convolutional long short-term memory layer;
        processing output from the convolutional long short-term memory layer for a sequentially last of the plurality of two-dimensional slices to generate a probability of the disease;
            comparing the probability to the label;
            updating the disease detection model based on the comparison; and
    after the disease detection model is trained, applying the disease detection model to a new image study including a sequence of a plurality of two-dimensional slices of a three-dimensional image volume to generate a probability of the disease for the new image study.

19. The non-transitory computer-readable medium of claim 18, wherein the probability of the disease is a probability of emphysema and wherein the plurality of two-dimensional slices include a series of computed tomography (CT) images including a chest.

20. The non-transitory computer-readable medium of claim 18, wherein the three-dimensional image volume does not include any annotations.

* * * * *